United States Patent
Stocks

(10) Patent No.: US 8,498,512 B2
(45) Date of Patent: Jul. 30, 2013

(54) CONTROLLING BEAM INTENSITY IN AN OPHTHALMIC FIBER OPTIC ILLUMINATION SYSTEM USING ROTATABLE PLATE ARRAYS

(75) Inventor: David John Stocks, Royston (GB)

(73) Assignee: Bausch & Lomb Incorporated, Rochester, NY (US)

( * ) Notice: Subject to any disclaimer, the term of this patent is extended or adjusted under 35 U.S.C. 154(b) by 958 days.

(21) Appl. No.: 12/341,484

(22) Filed: Dec. 22, 2008

(65) Prior Publication Data

US 2010/0157622 A1    Jun. 24, 2010

(51) Int. Cl.
*G02B 6/00*      (2006.01)
(52) U.S. Cl.
USPC ........................................................... 385/140
(58) Field of Classification Search
USPC ............................................................. 385/140
See application file for complete search history.

(56) References Cited

U.S. PATENT DOCUMENTS

| | | | |
|---|---|---|---|
| 2,995,997 A | | 8/1961 | Cornelis |
| 5,006,965 A | * | 4/1991 | Jones ............................ 362/552 |
| 5,642,456 A | * | 6/1997 | Baker et al. ................... 385/140 |
| 2008/0225233 A1 | * | 9/2008 | Dacquay et al. .............. 351/213 |
| 2008/0246919 A1 | * | 10/2008 | Smith ............................ 351/213 |

OTHER PUBLICATIONS

International Search Report (PCTISA/210) and Written Opinion (PCT/ISA/237) mailed on Dec. 23, 2010.

* cited by examiner

*Primary Examiner* — Uyen Chau N Le
*Assistant Examiner* — Hoang Tran
(74) *Attorney, Agent, or Firm* — Jeffrey B. Powers

(57) ABSTRACT

An ophthalmic illumination system includes a collimated light beam focused onto an optical fiber for transmission of the light beam to an ophthalmic light probe. A light attenuator includes a pair of arrays positioned serially in a path for the collimated beam. The arrays are movable in parallel in the path about a rotational axis orthogonal to the path and between the arrays. Each array includes a plurality of regularly spaced-apart parallel plates, the parallel plates of one array being non-parallel to the plates of the other array.

12 Claims, 2 Drawing Sheets

CONTROLLING BEAM INTENSITY IN AN OPHTHALMIC FIBER OPTIC ILLUMINATION SYSTEM USING ROTATABLE PLATE ARRAYS

FIELD

The present disclosure relates to ophthalmic illumination systems and more particularly to an ophthalmic illumination system in which a plurality of arrays of parallel plates are rotated in a collimated beam to control intensity of the beam.

BACKGROUND

This section provides background information related to the present disclosure which is not necessarily prior art.

When ophthalmic surgery is performed, an ophthalmic illumination system is used to illuminate the interior of a patient's eye so that the surgeon may view the surgical site. In a typical ophthalmic illumination system, light is collected, collimated and focused onto an entrance pupil of optical fiber connected to an opto-illuminator, or light probe. A tip of the probe is inserted into an incision in the eye. A number of mechanical shutter devices have been used to control the light output to a desired level at the surgical site.

SUMMARY

This section provides a general summary of the disclosure, and is not a comprehensive disclosure of its full scope or all of its features.

In one configuration, the present disclosure is directed to an ophthalmic illumination system. A collimated light beam may be focused onto an optical fiber for transmission to an ophthalmic light probe. A light attenuator includes a pair of arrays positioned serially in a path for the collimated beam. The arrays are movable in parallel in the path about a rotational axis orthogonal to the path and between the arrays. Each array includes a plurality of regularly spaced-apart parallel plates, the parallel plates of one array being non-parallel to the plates of the other array.

In another configuration, the disclosure is directed to an ophthalmic illumination system including a light source and light collection optics through which a beam from the light source may be collimated and focused for transmission to an ophthalmic light probe. A light attenuator in the light collection optics includes a pair of parallel arrays positioned serially in a path for the collimated beam and rotatable together in the path about an axis orthogonal to the path and between the arrays. Each array includes a plurality of regularly spaced-apart parallel plates, the parallel plates of one array orthogonal to the plates of the other array.

in yet another implementation, the disclosure is directed to a method of using a light attenuator in an ophthalmic illumination system. The method includes rotating a pair of arrays of the attenuator in parallel about an axis in a path for the collimated beam. The arrays are positioned serially in the path, the axis orthogonal to the path. The rotating is performed until a plurality of regularly spaced-apart parallel plates of each array are selectively positioned in the collimated beam, the parallel plates of one array being non-parallel to the plates of the other array relative to the path.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
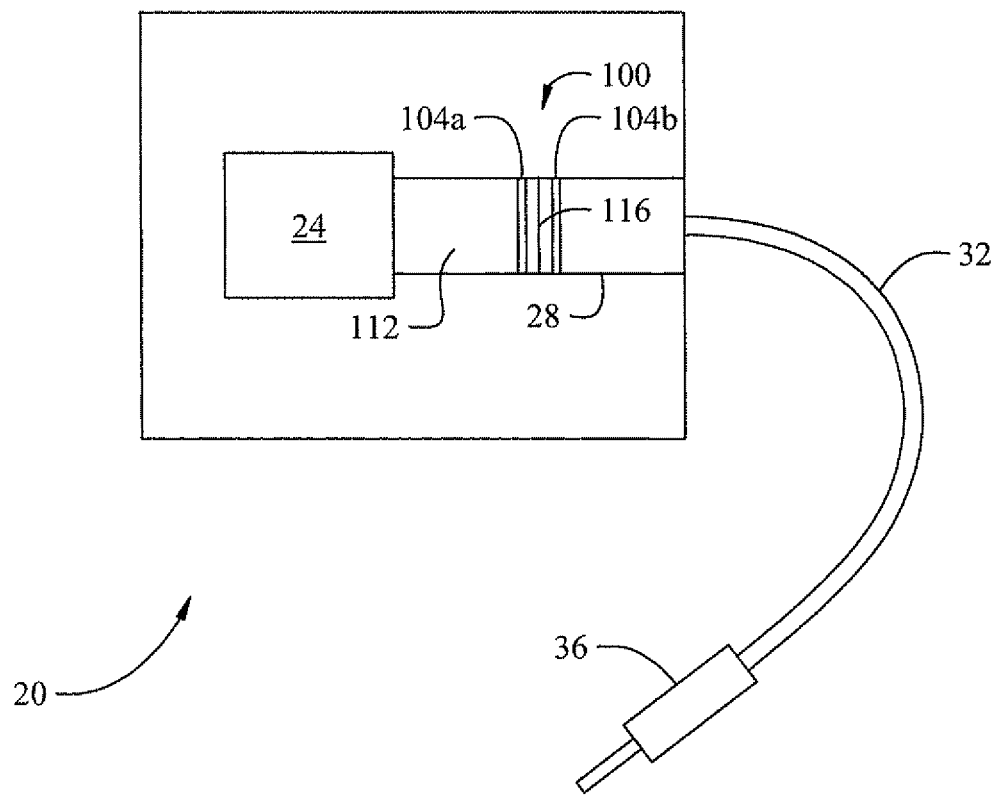
FIG. 1 is a diagram of an ophthalmic illumination system in accordance with one implementation of the disclosure.
Figure 2A:
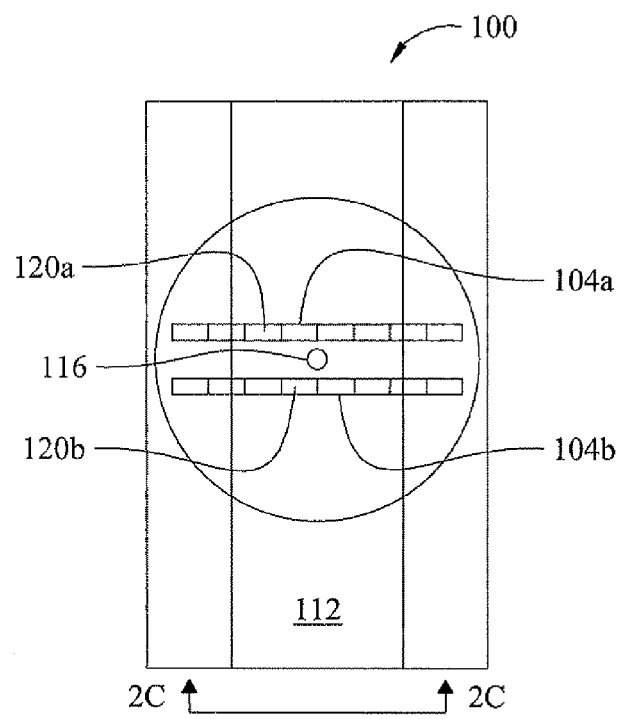
FIG. 2A is a top cross-sectional view of arrays of a light attenuator in accordance with one implementation of the disclosure, the arrays positioned in a fully open configuration of the attenuator.
Figure 2B:
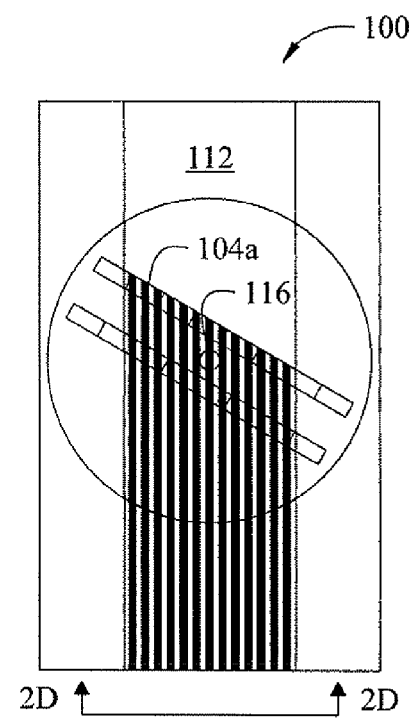
FIG. 2B is a top cross-sectional view of the arrays shown in FIG. 2A, the arrays positioned at a 45-degree angle to a light path through the attenuator.
Figure 2C:
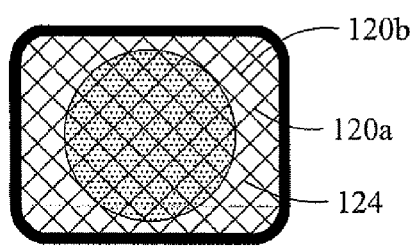
FIG. 2C is a view of the arrays positioned in the light path as shown in FIG. 2A, the view taken along lines 2C-2C from a distal end of the light path.
Figure 2D:
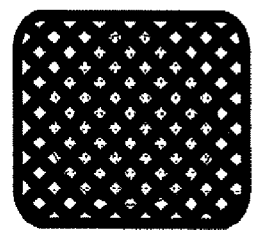
FIG. 2D is a frontal view of the arrays positioned in the light path as shown in FIG. 2B, the view taken along lines 2D-2D from a distal end of the light path.

A diagram of an ophthalmic illumination system in accordance with one implementation of the disclosure is indicated generally in FIG. 1 by reference number 20. A light source 24 provides light that is collected, collimated, and refocused via light collection optics 28 for transmission through an optical fiber 32 to a light probe 36. The light source 24 may be, for example, a xenon arc lamp, a filament lamp or other type of light source.

One configuration of a light attenuator, indicated generally by reference number 100, is provided in the light collection optics 28. The attenuator 100 includes a pair of parallel arrays 104a and 104b positioned in a path 112 for a collimated beam. The arrays 104a and 104b are rotatable to control intensity of the beam. More specifically, the arrays are rotatable together in the path 112 about an axis 116 between the arrays.

The attenuator 100 is shown in greater detail in FIGS. 2A through 2D. The arrays 104a and 104b are positioned serially in the path 112 for the collimated beam. The arrays 104a and 104b are movable in parallel in the path 112 about the rotational axis 116, which is orthogonal to the path 112. The arrays 104a and 104b respectively include a plurality of regularly spaced-apart parallel plates 120a and 120b, shown more clearly in profile in FIGS. 2C and 2D. The parallel plates 120a of the array 104a are non-parallel to the plates 120b of the array 104b. Specifically and for example, the plates 120a of the array 104a are substantially orthogonal to the plates 120b of the array 104b. In various implementations, the parallel plates of at least one of the arrays 104a and 104b are at a 45-degree angle to the rotational axis 116. For example, the plates 120a and 120b of both arrays 104a and 104b are at 45-degree angles to the axis 116.

Each array (104a, 104b) passes a fraction of light incident on the array, dependent on an angle of rotation of the axis 116. In the present configuration in which plates of the arrays 104a and 104b are substantially orthogonal, a total amount of light passing the arrays is approximately equal to the square of an amount of light passing through one of the arrays 104a and 104b. For example, if each of the arrays (104a, 104b) is positioned to pass twenty percent (20%) of light incident on it, then a total light output is approximately four percent (4%) (i.e., 0.2×0.2=0.04).

In some implementations of the disclosure, a method is provided for using a light attenuator in an ophthalmic illumination system. For example, and referring to the attenuator 100, a user rotates the arrays 104a and 104b in parallel about the rotational axis 116 until the plates (120a, 120b) of each array are selectively positioned in the light path 112. In this way each plate of each array blocks an amount of a light beam based on an angle of rotation of the plates about the rotational axis. To place the attenuator 100 in a substantially fully open position, the user rotates the arrays 104a and 104b to present edges 124 of each plate (120a, 120b) to a beam in the light path 112. Each array (104a, 104b) can be selectively positioned together with the other array, so that each array passes a selected percentage of the beam to obtain a total light output equal to the square of the selected percentage.

Attenuators configured in accordance with the disclosure can have manufacturing tolerances considerably larger than those of prior art attenuator configurations. In some prior art attenuators in which parallel plate arrays are used, it can be difficult to meet manufacturing tolerances and still achieve a light output that is homogeneous at low output levels. In attenuator configurations in accordance with the disclosure, however, larger tolerances can be allowed. This is due in part to rotating the arrays such that a shadow of each plate overlaps with an adjacent plate to obtain a minimum light output level through the attenuator. For example, where plates of a width of 2.3 millimeters and 1.5-millimeter gaps are provided between adjacent plates 120a of the array 104a and also between adjacent plates 120b of the array 104b, a gap of about 300 micrometers between any two adjacent plates of an array 104a or 104b can be provided to pass light at a low light output level of five percent (5%). Thus manufacturing tolerances are considerably easier to meet than in prior art systems.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of a device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An ophthalmic illumination system comprising:
an optical fiber onto which a collimated light beam may be focused for transmission to an ophthalmic light probe;
a light attenuator including a pair of arrays positioned serially in a path of the collimated beam, the arrays movable in parallel in the path about a rotational axis orthogonal to the path and between the arrays; and
each array including a plurality of regularly spaced-apart parallel plates, the parallel plates of one array being non-parallel to the plates of the other array.

2. The system of claim 1, wherein the parallel plates of one array are orthogonal to the plates of the other array.

3. The system of claim 1, wherein the plates of one of the arrays are separated from one another by 1.5 millimeters, and a width of the plates is 2.3 millimeters.

4. The system of claim 1, wherein each array passes an amount of the beam based on an angle of rotation of the arrays about the rotational axis.

5. The system of claim 1, wherein the plates of each array block an amount of the beam based on an angle of rotation of the plates about the rotational axis.

6. The system of claim 1, wherein the parallel plates of at least one of the arrays are at a 45-degree angle relative to the rotational axis.

7. An ophthalmic illumination system comprising:
a light source;
light collection optics through which a beam from the light source may be collimated and focused for transmission to an ophthalmic light probe;
a light attenuator in the light collection optics, the attenuator including a pair of parallel arrays positioned serially in a path of the collimated beam and rotatable together in the path about an axis orthogonal to the path and between the arrays; and
each array including a plurality of regularly spaced-apart parallel plates, the parallel plates of one array orthogonal to the plates of the other array.

8. The system of claim 7, wherein an edge of each plate is presented to the beam when the attenuator is in a substantially fully open position.

9. The system of claim 7, wherein the plates of one of the arrays are separated from one another by about 1.5 millimeters, and a width of the plates is 2.3 millimeters.

10. The system of claim 7, wherein each array passes an amount of the beam based on an angle of rotation of the array.

11. The system of claim 7, wherein the plates of each array blocks an amount of the beam based on an angle of rotation of the plates.

12. The system of claim 7, wherein the parallel plates of the arrays are at 45-degree angles to the axis.

* * * * *